US00PP23020P3

(12) United States Plant Patent
Korlipara

(10) Patent No.: US PP23,020 P3
(45) Date of Patent: Sep. 4, 2012

(54) ***ECHINACEA* PLANT NAMED 'CRANBERRY CUPCAKE'**

(50) Latin Name: ***Echinacea* spp.**
Varietal Denomination: Cranberry Cupcake

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 94 days.

(21) Appl. No.: 12/931,237

(22) Filed: Jan. 26, 2011

(65) Prior Publication Data

US 2012/0192327 P1 Jul. 26, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Cranberry Cupcake' characterized by rose pink ray florets, enlarged cranberry pink disc florets forming an anemone-type inflorescence, a dwarf habit with strong stems, and excellent vigor.

1 Drawing Sheet

Botanical denomination: *Echinacea* spp.

Variety designation: 'Cranberry Cupcake'.

The present invention relates to a new and distinct cultivar of *Echinacea* and given the cultivar name 'Cranberry Cupcake'. *Echinacea* is in the family Asteraceae. This new cultivar is a third generation seeding originating from a planned breeding program using *Echinacea purpurea* 'Razzmatazz' (U.S. Plant Pat. No. 13,894) as the seed parent in the original cross and unnamed proprietary, unreleased interspecific hybrids for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety has a much more compact habit.

Compared to *Echinacea purpurea* 'Pink Double Delight' (U.S. Plant Pat. No. 18,803), the new cultivar is shorter with a higher crown count, and has fuller inflorescences with more ray florets.

This new *Echinacea* cultivar is distinguished by:

1. rose pink ray florets,
2. enlarged cranberry pink disc florets forming an anemone-type inflorescence,
3. a multicrown, dwarf habit with strong stems, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the inflorescences and habit of *Echinacea* 'Cranberry Cupcake' as a one and one-half-year-old in the trial field in full sun in late July in Canby, Oreg.

FIG. 2 shows the same age plant later in full bloom in the garden.

DETAILED PLANT DESCRIPTION

The following is a detailed description of the new *Echinacea* cultivar based on observations of a 1 and one-half-year-old specimens growing in the ground in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 53 cm wide and 40 cm tall to top of inflorescences.
*Form.*—Basal clump, with about 50 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 0 to 3 flowering branches off the main flowering stems.
*Size.*—To 38 cm tall to a terminal inflorescence and 6 mm wide at base.
*Internode length.*—1.5 cm to 6 cm.
*Surface texture.*—Strigose.
*Color.*—Yellow Green 145A mottled Yellow Green 146A.

Leaf (basal):

*Type.*—Simple.
*Shape.*—Lanceolate.
*Arrangement.*—Basal.
*Blade size.*—Grows to 11.5 cm long and 4 cm wide.
*Margins.*—Sparsely serrate, slightly undulate.
*Apex.*—Acute.

*Base.*—Attenuate.
*Surface texture.*—Strigose on both sides.
*Venation.*—Pinnate.
*Color.*—Closest to: topside, Green 137A, bottom side Yellow Green 147B.
*Petiole description.*—Grows to 9.5 cm long and 2 mm wide, strigose, Yellow Green 147C.

Leaf (stem):
*Type.*—Simple.
*Shape.*—Ovate to lanceolate.
*Arrangement.*—Alternate.
*Blade size.*—Grows to 13 cm long and 3.2 cm wide.
*Margins.*—Sparsely serrate, slightly undulate.
*Apex.*—Acuminate.
*Base.*—Attenuate.
*Surface texture.*—Strigose on both sides.
*Venation.*—Pinnate, with 3 main veins from the base.
*Color.*—Topside, Yellow Green 147A, bottom side Yellow Green 147B.
*Petiole description.*—On lower leaves only, clasping, grows to 9 cm long and 4 mm wide above the clasp, strigose, Yellow Green 146C.

Inflorescence:
*Type.*—Composite on terminal stalked heads.
*Number of flowering stems per plant.*—About 50.
*Flowering stem.*—Grows to 38 cm tall from the base of the plant to the terminal inflorescence and can grow to 14 cm long from the top stem leaf to the base of an inflorescence; sometimes branched, with 1 to 4 inflorescences per stem; diameter growing to 6 mm wide near the inflorescence; strigose; Yellow Green 145A mottled Yellow Green 146A.
*Size.*—Grows to 8 cm wide and 4.5 cm deep as disc enlarges.
*Form.*—Ray florets held slightly reflexed, mature disc is conic.
*Immature inflorescence.*—Grows to 3 cm wide and 1.5 cm deep, ray florets held slightly upright and rolled up so only the back color shows, Orange White 159B with tints of Greyed Purple 185B, disc color two toned Yellow Green 147B and Greyed Purple 187C.
*Ray florets.*—Without pistil or stamen, about 22 full size and about 5 to 10 undersize, full size florets grow to 40 mm long and 6 mm wide, oblanceolate with the tip two toothed (each acute), entire margins, base attenuate, glabrous on both sides; topside color Red Purple 70C maturing to 70B, bottom side Greyed Purple 186C.
*Disc.*—Flat becoming conic, becoming 25 mm deep and 60 mm wide with maturity, overall color is Red Purple 64A.
*Disc florets.*—About 400 in number, each with 1 pistil and 4 stamen, grow to 22 mm long and 5 mm wide, each with one persistent bract (11 mm long with the top 2 mm colored Greyed Purple 187A on tip then 1 mm Orange Red 32A, then Yellow Green 148D to lower 6 mm White NN155B); showy 3 to 5 lobed corollas to 18 mm long and 5 mm wide, tubular on the bottom with the lobes spread out like a fan, glabrous, back side color Red Purple 59A on lobes lightening to White NN155B at base, inside color Red Purple 64A on lobes to 64D at base; pistil 10 mm long, ovary 4 mm long, White NN155A, style 5 mm long Grayed Purple 186D, 2-branched stigma spreading 1.5 mm wide, Greyed Purple 187A; stamen 5 mm long, anthers 2.5 mm long and Greyed Purple N186A, filaments 2.5 mm long, White 155A, very little pollen, Orange 26B.
*Phyllaries.*—In 4 leafy series, area 3 cm wide and 5 mm deep, lobes lanceolate in shape, reflexed, grow to 11 mm long and 3 mm wide, Yellow Green 146B, margins strigose, tip acute, strigose on both sides.
*Receptacle.*—Grows to 13 mm wide and 10 mm deep, White 155A.
*Bloom period.*—July through October in Canby, Oreg.
*Fragrance.*—Light, floral.
*Lastingness.*—Each inflorescence lasts about two weeks in Canby, Oreg.

Seeds: None seen.
*Fertility.*—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

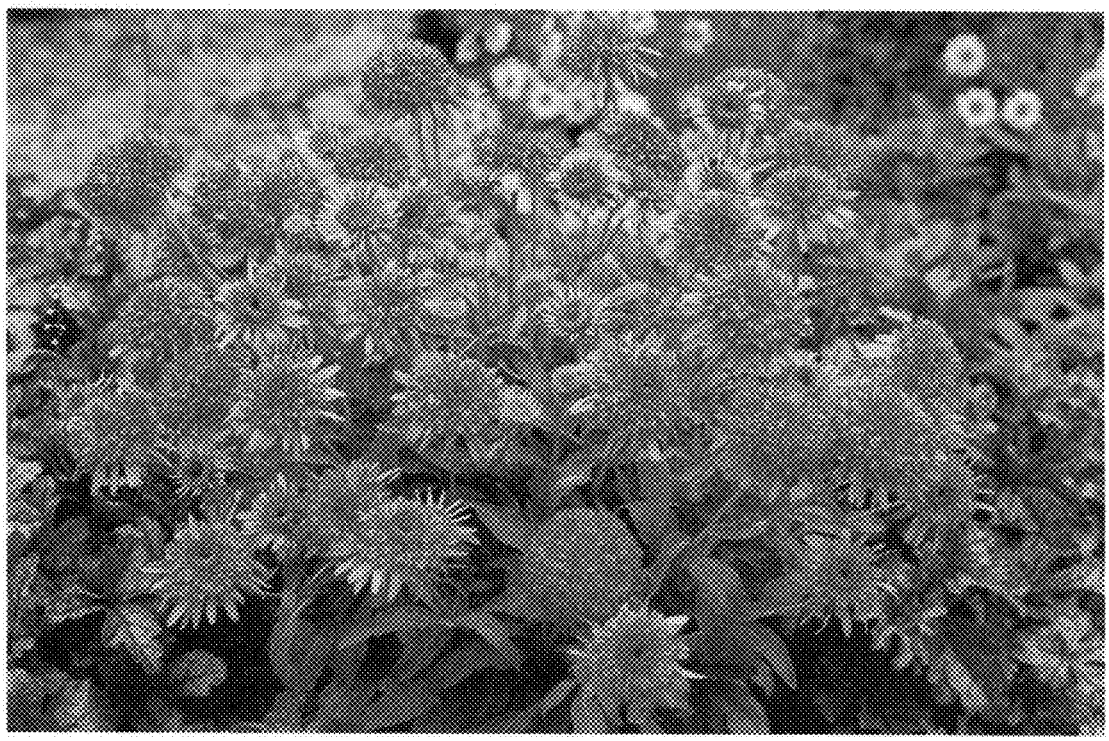

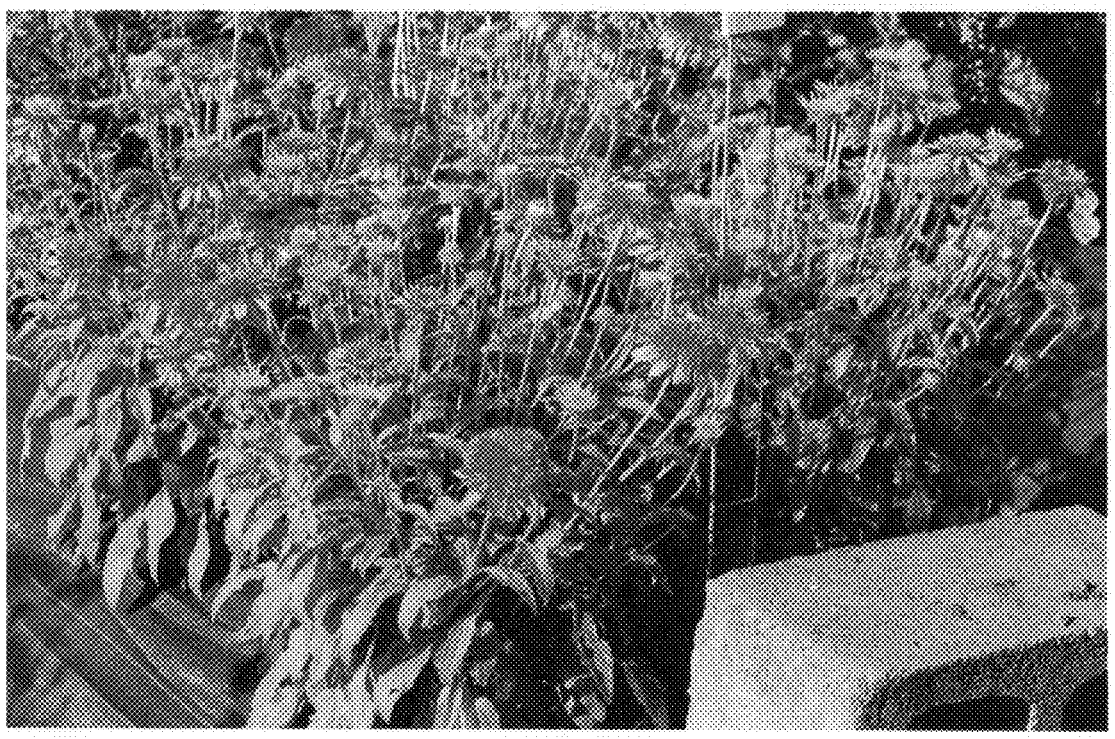
Figure 1 above
Figure 2 below